United States Patent
Kopetsch

(10) Patent No.: US 8,629,190 B2
(45) Date of Patent: Jan. 14, 2014

(54) PROCESS AND PLANT FOR PRODUCING METHANOL

(75) Inventor: Hans Kopetsch, Bad Homburg (DE)

(73) Assignee: Lurgi GmbH, Frankfurt am Main (DE)

( * ) Notice: Subject to any disclaimer, the term of this patent is extended or adjusted under 35 U.S.C. 154(b) by 316 days.

(21) Appl. No.: 13/121,553

(22) PCT Filed: Jul. 29, 2009

(86) PCT No.: PCT/EP2009/005484
§ 371 (c)(1),
(2), (4) Date: Mar. 29, 2011

(87) PCT Pub. No.: WO2010/037441
PCT Pub. Date: Apr. 8, 2010

(65) Prior Publication Data
US 2011/0178187 A1    Jul. 21, 2011

(30) Foreign Application Priority Data
Sep. 30, 2008   (DE) .......................... 10 2008 049 622

(51) Int. Cl.
    *C07C 27/00*   (2006.01)
(52) U.S. Cl.
    USPC ........................... 518/706; 518/700; 518/705
(58) Field of Classification Search
    USPC ......................................... 518/700, 705, 706
    See application file for complete search history.

(56) References Cited

U.S. PATENT DOCUMENTS

| 4,968,722 A | 11/1990 | Westerterp |
| 5,216,034 A | 6/1993 | Sie |
| 5,827,901 A | 10/1998 | König et al. |
| 2007/0293590 A1 | 12/2007 | Hipp |

FOREIGN PATENT DOCUMENTS

FR    2533554    3/1984

OTHER PUBLICATIONS

PCT Notification Concerning Transmittal of International Preliminary Report on Patentability, from International Application No. PCT/EP2009/005484, corresponding to U.S. Appl. No. 13/121,553, mailed Apr. 4, 2011, pp. 1-9.
PCT International Search Report from International Application PCT/EP2009/005484, mailed Nov. 9, 2009, 2 pages.

*Primary Examiner* — Jafar Parsa
(74) *Attorney, Agent, or Firm* — Pauly, Devries Smith & Deffner, L.L.C.

(57) ABSTRACT

For producing methanol from a synthesis gas containing hydrogen and carbon oxides the synthesis gas is passed through a first, preferably water-cooled reactor in which a part of the carbon oxides is catalytically converted to methanol, and the resulting mixture containing synthesis gas and methanol vapor is supplied to a second, preferably gas-cooled reactor in which a further part of the carbon oxides is converted to methanol. The mixture withdrawn from the first reactor is guided through a gas/gas heat exchanger in which the mixture is cooled to a temperature below its dew point. Subsequently, methanol is separated from the gas stream in a methanol separator and withdrawn, while the remaining gas stream is supplied to the second reactor.

5 Claims, 1 Drawing Sheet

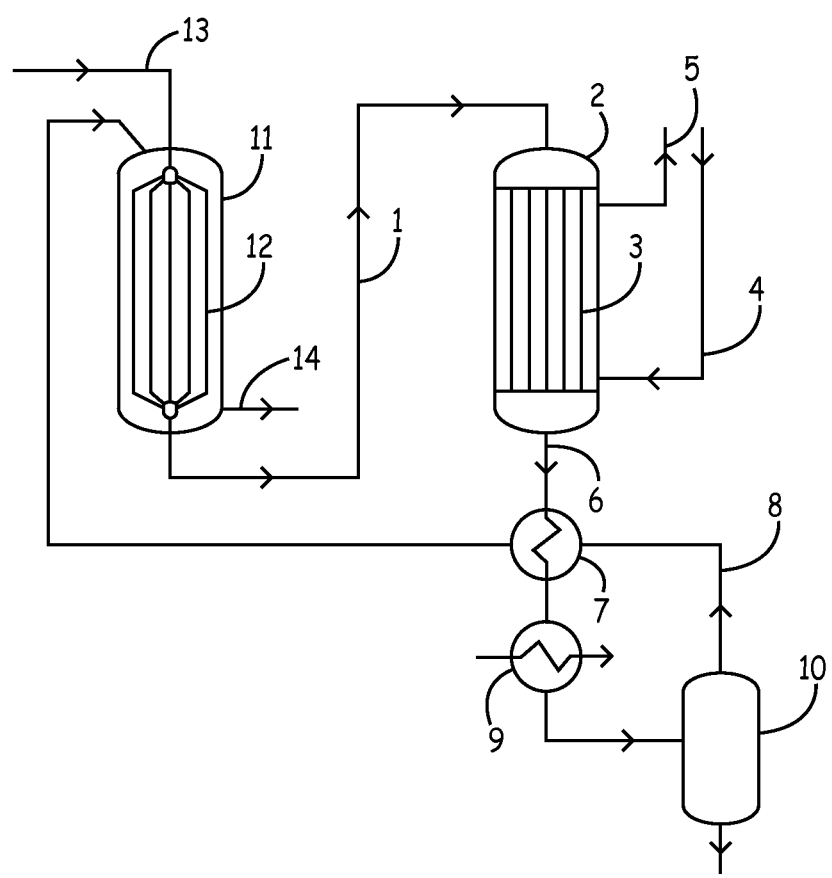

US 8,629,190 B2

PROCESS AND PLANT FOR PRODUCING METHANOL

CROSS-REFERENCE TO RELATED APPLICATIONS

This application is a national stage application under 35 U.S.C. 371 of International Patent Application Serial No. PCT/EP2009/005484, entitled "Process and Plant for Producing Methanol," filed Jul. 29, 2009, which claims priority from German Patent Application No. 10 2008 049 622.7, filed Sep. 30, 2008.

FIELD OF THE INVENTION

This invention relates to the production of methanol from a synthesis gas containing hydrogen and carbon oxides, wherein the synthesis gas is passed through a first, preferably water-cooled reactor in which a part of the carbon oxides is catalytically converted to methanol, and wherein the resulting mixture containing synthesis gas and methanol vapor is supplied to a second, preferably gas-cooled reactor in which a further part of the carbon oxides is converted to methanol.

BACKGROUND OF THE INVENTION

Processes for producing methanol are known for example from EP 0 790 226 B1. The methanol is produced in a cyclic process in which a mixture of fresh and partly reacted synthesis gas first is supplied to a water-cooled reactor and then to a gas-cooled reactor, in each of which the synthesis gas is converted to methanol on a copper-based catalyst. The methanol produced in the process is separated from the synthesis gas to be recirculated, which then is countercurrently passed through the gas-cooled reactor as coolant and preheated to a temperature of 220 to 280° C., before it is introduced into the first synthesis reactor. Novel, more active catalyst generations allow an operation of the methanol production at lower and lower temperatures, which results in a better exploitation of the thermodynamic potential of the reaction and in a higher methanol yield. In this connection, it must be prevented that a condensation of the methanol product occurs in the gas-cooled second reactor, since the reactor wall temperature at the outlet can approach the dew point of the product gas.

FR 2,533,554 A1 describes a process for producing alcohols from synthesis gas in two reactor stages, wherein from the product of the second reactor stage a liquid fraction rich in methanol and higher alcohols is separated from the gas stream by condensation. The gas stream is at least partly recirculated to the first reactor stage, in order to increase the ratio $H_2/CO$ to a value≥1.8. An intermediate condensation of methanol between the two reactor stages should be avoided, in order to reduce the water content of the mixture obtained and thereby facilitate the future dehydrogenation of the alcohols.

From the U.S. Pat. No. 4,968,722 a process for producing methanol is known, in which the methanol product is removed by absorption between two reactor stages, in order to thereby increase the product yield of the equilibrium reaction in the second reactor stage. An intermediate condensation here is also described as disadvantageous, since it requires large heat exchanging surfaces.

EP 0 483 919 A2 describes a process for methanol production, in which the conversion of the synthesis gas is effected in a plurality of series-connected fluidized-bed reactors, wherein between the reactor stages a separation of methanol formed is effected by cooling and condensation.

The document US 2007/0293590 A1 describes the performance of heterogeneously catalytic exothermal gas phase reactions for the methanol synthesis from a synthesis gas in at least two series-connected synthesis reactors. Between these reactors a partial stream of the methanol-containing product is withdrawn and methanol is condensed out by multistage heat exchange with boiler feed water and deionized water. The gaseous constituents are mixed with the warm part of the product gas from the first reactor and supplied to the second reactor.

SUMMARY OF THE INVENTION

It is the object of the invention to reliably avoid the condensation of methanol at the second reactor in particular when using highly active catalysts.

This object substantially is solved with the invention in that the partly reacted mixture withdrawn from the first reactor is guided through a gas/gas heat exchanger, in which the mixture is cooled to a temperature below its dew point, that methanol is separated from the gas stream in a methanol separator and withdrawn, and that after being reheated, preferably in said gas/gas heat exchanger, the remaining gas stream is supplied to the second reactor.

The dew point of the mixture entering the second reactor substantially depends on the methanol concentration. By separating the methanol obtained in the first reaction stage, the dew point of the mixture is lowered distinctly down to about 40° C. (namely the temperature in the methanol separator located before the same), so that there is no risk of a methanol condensation in the second reactor, since the distance of the temperature of the reactor components from the dew point also is sufficiently large at the outlet of the second reactor, in order to reliably avoid that the temperature falls below the dew point. At the same time, the methanol yield of the second reactor stage can be increased, since the reaction equilibrium is shifted to the product side and/or a higher reaction potential is created for the conversion of the gas in the second reactor.

In accordance with a preferred aspect of the invention the mixture obtained from the first reactor is cooled down as deep as possible, in particular to a temperature in the range from 30 to 70° C., in at least one further heat exchanger, before introduction into the methanol separator. By further cooling of the reactor outlet gas, the condensation of the methanol produced in the first stage is intensified. Even if the temperature in the gas/gas heat exchanger has fallen below the dew point of the mixture, the gas/liquid mixture is further cooled to temperatures achievable with air or water coolers, in order to condense as much methanol as possible out of the gas phase and subsequently separate the same in a gas/liquid separator.

A particularly economic utilization of the plant is achieved when the gas stream withdrawn from the methanol separator is preheated in the gas/gas heat exchanger, before it is supplied to the second reactor. The heat thereby is retained in the system and utilized for the necessary heating of the gas stream to the required reaction temperature in the second reactor.

The invention also extends to a plant for producing methanol from a synthesis gas containing hydrogen and carbon oxides, which is suitable for performing the process described above. The plant comprises a first, preferably water-cooled reactor in which a part of the carbon oxides is catalytically converted to methanol, a second, preferably gas-cooled reactor to which the gas mixture obtained from the first reactor is supplied via a conduit and in which a further part of the carbon oxides is converted to methanol, and a methanol separator for separating the methanol from the synthesis gas. In accordance with the invention a gas/gas heat exchanger for cooling the gas mixture obtained from the first reactor is provided subsequent to the first reactor.

In accordance with a development of this invention, at least one additional heat exchanger is provided between the gas/gas heat exchanger and the methanol separator for the further cooling of the gas mixture.

In accordance with the invention, a conduit leads from the methanol separator to the inlet of the second reactor, via which the separated synthesis gas is supplied to the second reactor for the further conversion. The conduit preferably is guided through the gas/gas heat exchanger, in order to preheat the synthesis gas to the required reaction temperature and at the same time achieve an optimum utilization of the thermal energy.

Further developments, advantages and possible applications of the invention can also be taken from the following description of an embodiment and the drawing. All features described and/or illustrated form the subject-matter of the invention per se or in any combination, independent of their inclusion in the claims or their back-reference.

BRIEF DESCRIPTION OF THE FIGURES

FIG. 1 schematically shows a plant for performing the process of the invention.

DETAILED DESCRIPTION

In the illustrated plant a mixture of fresh and recirculated synthesis gas is passed through a conduit 1 into a first synthesis reactor 2. This first reactor 2 preferably is a tubular reactor known per se, in which for example a copper-based catalyst is arranged in tubes 3. As coolant, water boiling under elevated pressure is used, which is supplied in conduit 4. A mixture of boiling water and steam is withdrawn in conduit 5 and supplied to a non-illustrated steam drum known per se for energy recovery.

The synthesis gas entering the first reactor 2 is preheated to a suitable temperature which is sufficient for the catalyst to respond. In this connection, it is also possible to first heat the synthesis gas only to a temperature below the response temperature of the catalyst and achieve the further preheating via the hot water jacket in the reactor. The water temperature then must of course lie above the response temperature of the catalyst. Usually, the gas temperature at the inlet of the first reactor 2 is about 180 to 250° C. and the pressure lies in the range from 2 to 12 MPa (20 to 120 bar), preferably in the range from 4 to 10 MPa (40 to 100 bar). The coolant which is withdrawn via conduit 5 usually has a temperature in the range from 220 to 280° C. Depending on the condition of the catalyst, 40 to 80% of the carbon oxides charged to the reactor 2 through conduit 1 are converted in an exothermal reaction in the first reactor 2.

From the first reactor 2, a first mixture substantially consisting of synthesis gas and methanol vapor is withdrawn via conduit 6, wherein the methanol content is 4 to 10 vol-%, mostly 5 to 8 vol-%. This mixture preferably is completely passed through a gas/gas heat exchanger 7, in order to lower the temperature below the dew point of methanol by heat exchange with synthesis gas recirculated via conduit 8. The dew point temperature substantially depends on the concentration of the methanol, and with a methanol concentration at the outlet of the first reactor 2 of e.g. 7 mol-% it is about 125° C.

Subsequent to the gas/gas heat exchanger 7, the gas/liquid mixture traverses at least one further heat exchanger 9, in order to further lower the temperature. This second heat exchanger preferably is air- or water-cooled. The gas/liquid mixture then is supplied to a methanol separator 10, in which the liquid methanol phase is separated from the gas phase. The largely methanol-free gas stream again is directly supplied to the gas/gas heat exchanger 7 via conduit 8 and heated to the inlet temperature of the next reaction stage.

Via conduit 8, the gas stream thus preheated is supplied to a second synthesis reactor 11 which for example is configured as a fixed-bed reactor provided with cooling tubes 12, which includes a copper-based catalyst. The catalyst preferably is provided on the shell side, but it can also be arranged in the tubes like in the first reactor 2.

In the second reactor 11, synthesis gas is used as cooling medium, which is supplied via conduit 13 with a temperature of 40 to 150° C. and flows through the second reactor 11 cocurrent to the gas stream from the first reactor 2, which is supplied via conduit 8 and preheated in the gas/gas heat exchanger 7. However, a countercurrent operation likewise is possible and also subject-matter of this invention. The temperature of the cooling gas at the inlet of the second reactor 11 results from the mixing ratio between recirculated and fresh synthesis gas and is chosen the lower the higher the reactivity of the gas stream supplied via conduit 8 into the second reactor 11. The synthesis gas used as coolant is preheated in the second reactor 11 and then flows through the conduit 1 to the first reactor 2.

The synthesis gas which enters the first reactor 2 should include hydrogen and carbon oxides approximately in the following proportions:
$H_2$=40 to 80 vol-%
$CO$=3 to 20 vol-% and
$CO_2$=1 to 20 vol-%.

A product mixture substantially containing synthesis gas and methanol vapor (second mixture) leaves the second reactor 11 through a conduit 14 and in a manner known per se flows through a non-illustrated cooler, whereby methanol is condensed. Subsequently, gases and liquid are separated in a separation tank and the crude methanol product is withdrawn and purified by distillation. By means of a condenser, the gases are passed as synthesis gas to be recirculated (recycle gas) via conduit 13 through the second reactor 11 and are passed on into the first reactor 2 after the resulting preheating. As is otherwise common practice, a part of the gases is removed from the cycle (purge), in order to limit the accumulation of inert components.

It should be appreciated that the design of the reactors 2, 11 as such is not limited to the variants described above. Rather, modifications of these reactors are also possible, for example as described in EP 0 790 226 B1.

LIST OF REFERENCE NUMERALS

1 conduit
2 first reactor
3 tubes
4 conduit
5 conduit
6 conduit
7 gas/gas heat exchanger
8 conduit
9 heat exchanger
10 methanol separator
11 second reactor
12 cooling tubes
13 conduit
14 conduit

The invention claimed is:

1. A process for producing methanol from a synthesis gas containing hydrogen and carbon oxides, wherein the synthesis gas is passed through a first reactor in which a part of the carbon oxides is catalytically converted to methanol, and wherein the resulting mixture containing synthesis gas and methanol vapor is supplied to a second reactor in which a further part of the carbon oxides is converted to methanol, wherein the mixture withdrawn from the first reactor is guided through a gas/gas heat exchanger in which the mixture is cooled to a temperature below its dew point, methanol is separated from the gas stream in a methanol separator and withdrawn, and the remaining gas stream is supplied to the second reactor, wherein the second reactor is configured as a fixed-bed reactor.

2. The process according to claim 1, wherein the mixture obtained from the first reactor is cooled down to a temperature in the range from 30 to 70° C., in at least one further heat exchanger, before introduction into the methanol separator.

3. The process according to claim 1, wherein the gas stream withdrawn from the methanol separator is preheated in the gas/gas heat exchanger, before it is supplied to the second reactor.

4. The process according to claim 1, wherein the first reactor is water cooled.

5. The process according to claim 1, wherein the second reactor is water cooled.

* * * * *